United States Patent [19]
Kuypers et al.

[11] Patent Number: 5,919,176
[45] Date of Patent: Jul. 6, 1999

[54] APPARATUS AND METHOD FOR COLLECTING BLOOD FROM AN UMBILICAL CORD

[75] Inventors: Franciscus A. Kuypers, El Cerrito; Robert B. Cole, Alamo; Richard P. Meyst, Valley Center; Lanny A. Gorton, San Diego; James I. Wright, Villa Park, all of Calif.

[73] Assignee: Children's Hospital Medical Center of Northern California, Oakland, Calif.

[21] Appl. No.: 08/742,438

[22] Filed: Oct. 30, 1996

Related U.S. Application Data

[60] Provisional application No. 60/017,402, May 14, 1996.

[51] Int. Cl.⁶ ........................................ A61M 1/00
[52] U.S. Cl. ...................... 604/317; 606/120; 606/119; 606/167
[58] Field of Search .................... 606/119, 120, 606/167; 604/317, 323; 600/573, 583

[56] References Cited

U.S. PATENT DOCUMENTS

| | | | |
|---|---|---|---|
| 4,781,188 | 11/1988 | Collins | 128/305 |
| 4,856,517 | 8/1989 | Collins et al. | 606/120 |
| 5,004,681 | 4/1991 | Boyse et al. | 435/2 |
| 5,053,025 | 10/1991 | Knippscheer | 604/317 |
| 5,114,672 | 5/1992 | Knippscheer et al. | 122/41 |
| 5,190,556 | 3/1993 | Hessel | 606/120 |
| 5,192,553 | 3/1993 | Boyse et al. | 424/529 |
| 5,342,328 | 8/1994 | Adelberg et al. | 604/317 |
| 5,356,373 | 10/1994 | Dracker | 604/4 |
| 5,372,481 | 12/1994 | Anderson | 604/32 |
| 5,415,665 | 5/1995 | Hessel et al. | 606/120 |
| 5,520,699 | 5/1996 | Hessel et al. | 606/120 |
| 5,575,796 | 11/1996 | King et al. | 606/120 |

FOREIGN PATENT DOCUMENTS

| | | |
|---|---|---|
| 0 438 626 A2 | 7/1991 | European Pat. Off. . |
| WO 91/09521 | 7/1991 | WIPO . |
| WO 92/03180 | 3/1992 | WIPO . |
| WO 92/16150 | 10/1992 | WIPO . |

OTHER PUBLICATIONS

Eder, Jerome M. and Gary R. Cutter, "A New Device for Collecting Core Blood," *Obstetrics & Gynecology*, vol. 86, No. 5, Nov., 1995, pp. 850–852.

*Primary Examiner*—Michael Buiz
*Assistant Examiner*—Tina T. D. Pham
*Attorney, Agent, or Firm*—Seed and Berry LLP

[57] ABSTRACT

An apparatus and method for collecting a large volume of blood from an umbilical cord in a sterile environment are shown and described. A housing having an inner region adapted to retain an umbilical cord in a desired location is provided, the housing having an opening through which the cord extends from the inner region of the housing to a region external to the housing. The cord is cut by a blade coupled to the housing, either by the motion of the blade from a first position to a second position, or by the movement of two portions of the housing from a first extended position to a second collapsed position. The newly cut end of the umbilical cord falls and hangs freely in the inner region of the housing, blood flowing from the placenta and umbilical cord via gravity into a blood collection region of the housing. The blood collection region may be flexible, and may be coupled to a conventional blood collection bag.

40 Claims, 9 Drawing Sheets

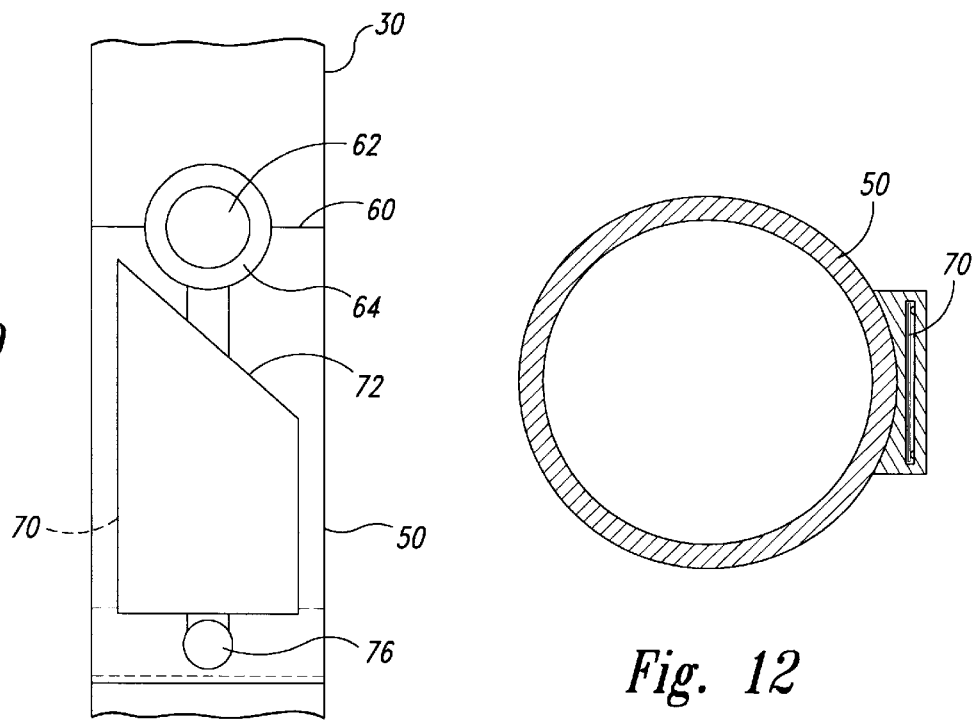
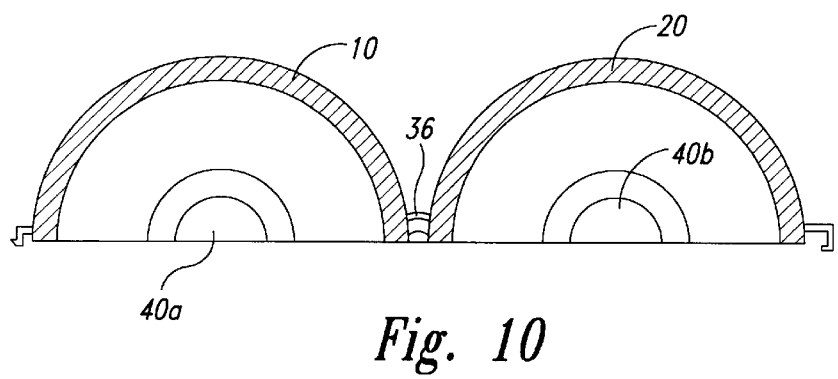
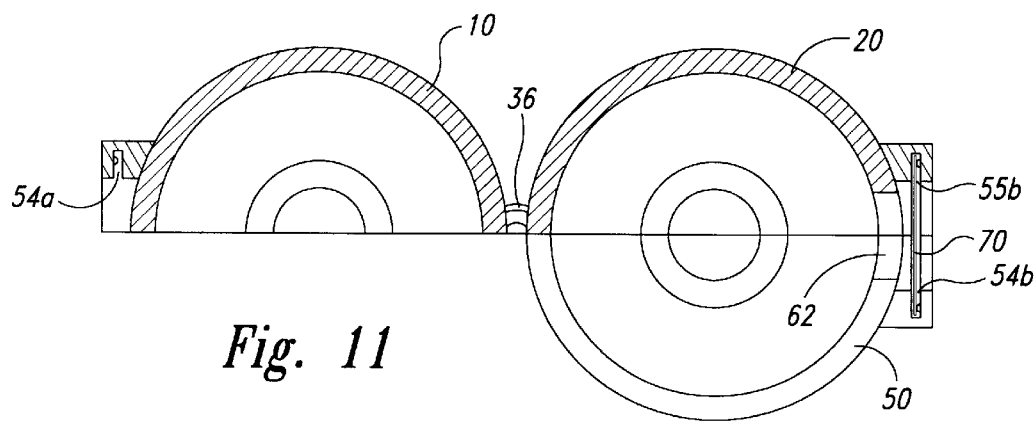

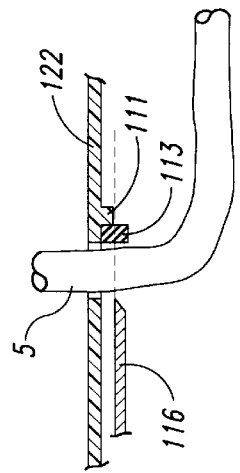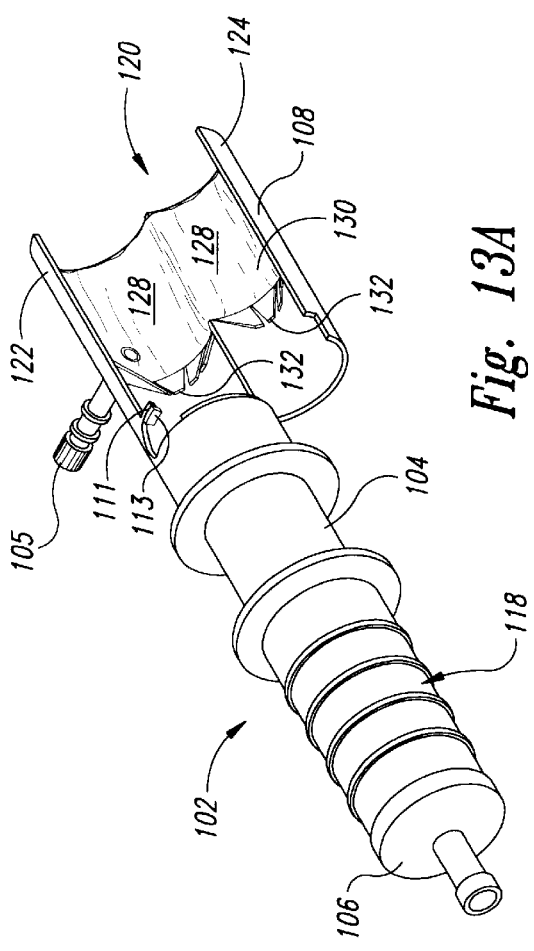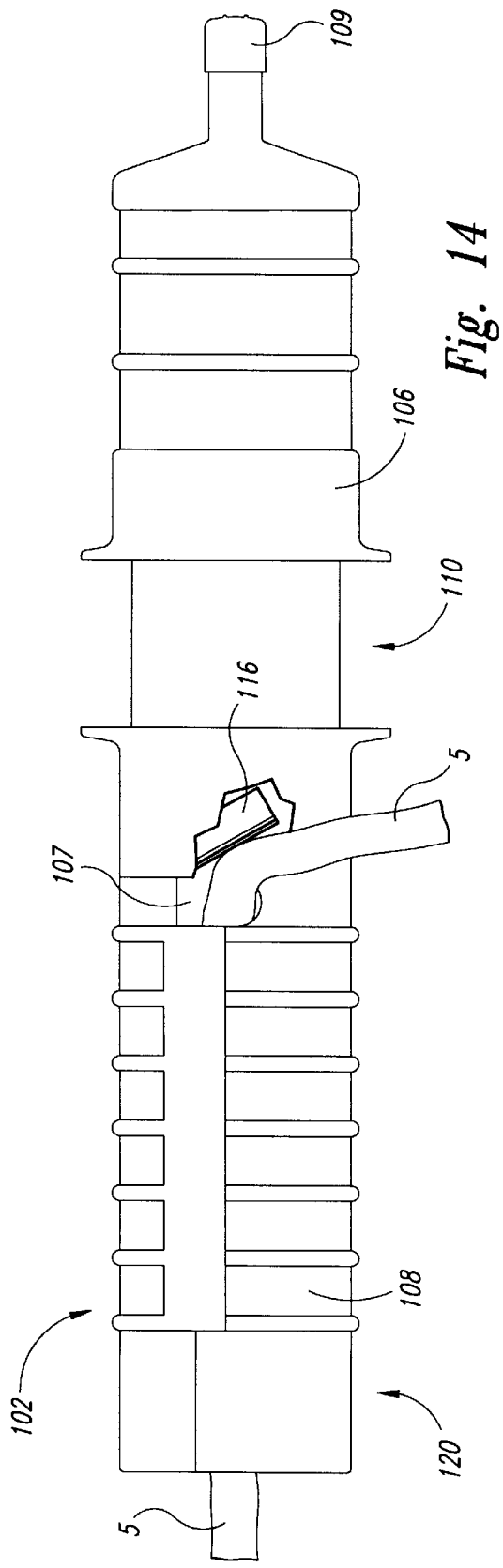

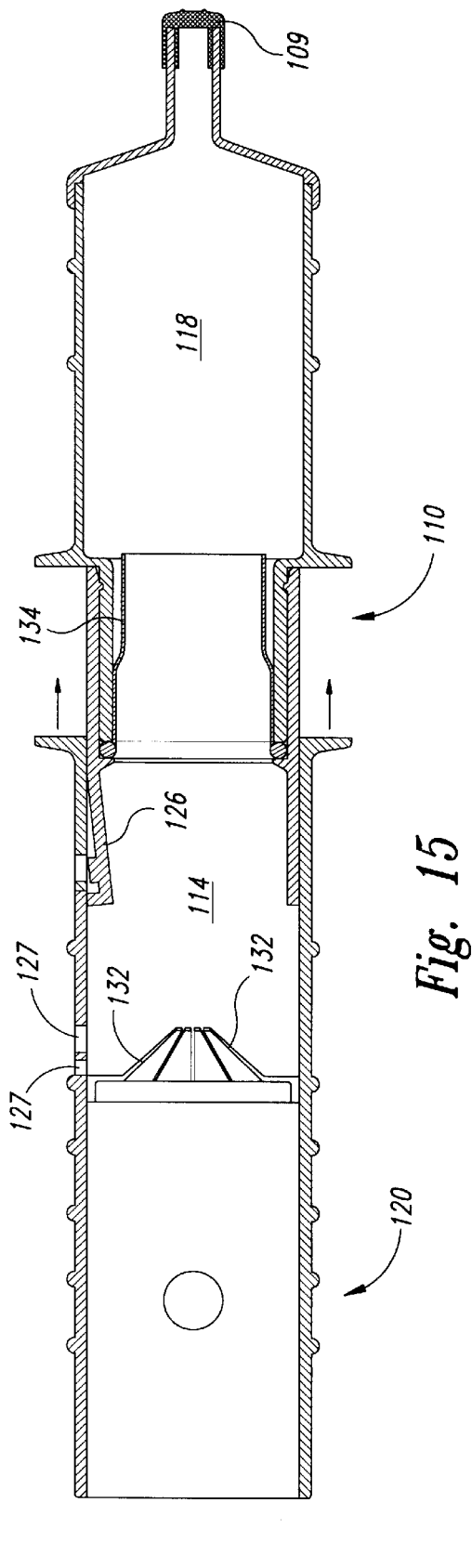
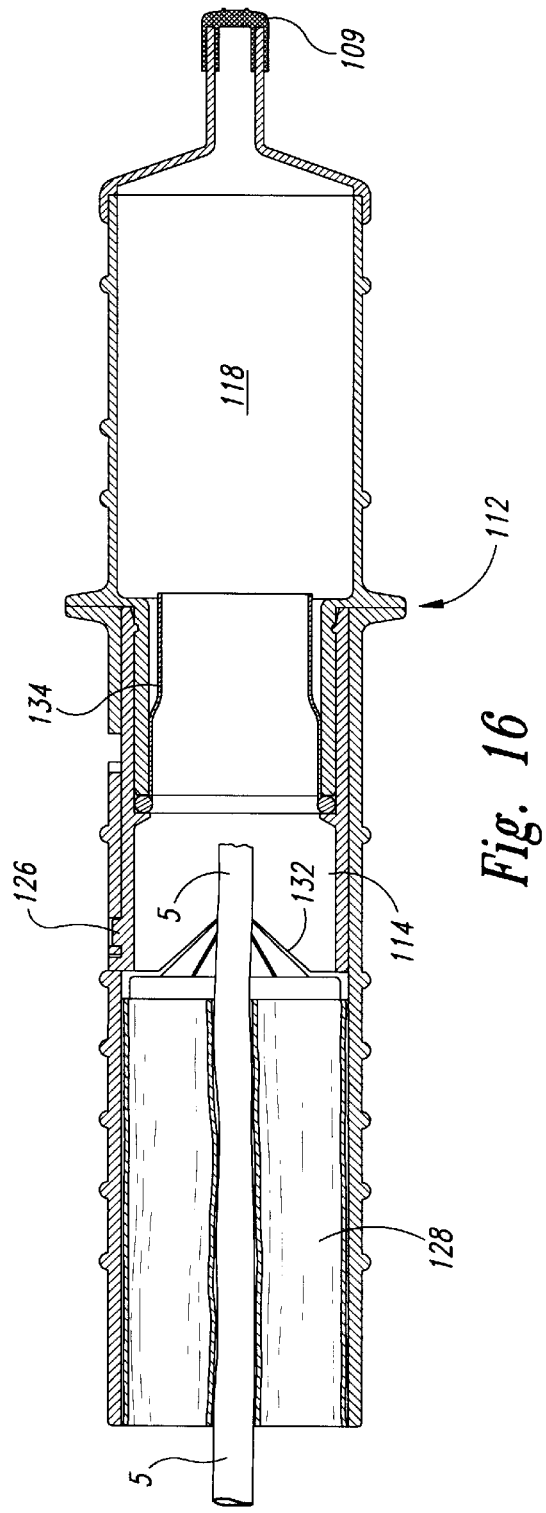

APPARATUS AND METHOD FOR COLLECTING BLOOD FROM AN UMBILICAL CORD

RELATED APPLICATIONS

This application claims the benefit of U.S. Provisional Application No. 60/017,402, filed May 14, 1996.

TECHNICAL FIELD

This invention is directed to an apparatus and method for collecting blood from an umbilical cord after delivery of a baby.

BACKGROUND OF THE INVENTION

Fetal blood is a source of numerous blood factors that have important commercial and therapeutic uses in a number of different fields, such as tissue culture, bone marrow transplantation, stem cell collection, pharmacology, and biologic research. While this need for fetal blood factors can be met for some purposes with non-human fetal blood (e.g., fetal calf serum is a common component of growth media used for mammalian cell cultures), some applications require the use of human fetal blood, principally due to biocompatability with the human immune system.

For example, although aggressive anti-cancer treatments systematically kill tumor cells, they also destroy blood-forming cells, namely, stem cells. Cancer patients undergoing aggressive therapy therefore require an infusion of stem cells to reconstitute their blood and immune system. Traditionally, bone marrow was thought to be the best source of stem cells, and gave rise to bone marrow transplantation. More recently, blood extracted from umbilical cords immediately following a child's birth has been identified as a rich and readily accessible source of stem cells.

Currently, the sole commercial source of human fetal blood is blood obtained from the placenta and umbilical cord of newborns after delivery. This blood is often referred to as "cord blood," as it is typically obtained by draining the placenta and umbilical cord through the severed umbilical cord after delivery.

At the present time, cord blood is typically collected by draining blood from a placenta into an open container by "milking" the umbilical cord. This rather crude procedure has several disadvantages in that it is awkward to perform and it is difficult to control the sterility of the collected cord blood. In another currently available method, blood is collected from the umbilical cord vein via a conventional large-gauge needle and syringe, although this procedure is also awkward to perform and exposes the medical personnel to potential needle sticks.

Accordingly, there is a need in the art for an improved apparatus and method for maximizing a volume of cord blood collected from an umbilical cord, in an aseptic manner, and in particular, a method and apparatus that are more simple and efficient to use. The present invention fulfills these needs, and provides further related advantages.

SUMMARY OF THE INVENTION

Briefly, the present invention provides an improved method and apparatus for collecting a large volume of blood from an umbilical cord, in an aseptic environment. In a preferred embodiment, a housing is provided, having a channel extending longitudinally through an upper, internal region of the housing, and an opening in communication with the channel and a region external to the housing. In use, shortly after the delivery of a baby and severing of the umbilical cord, the clamped, severed umbilical cord is placed in the housing such that it passes through the channel and extends through the opening. In a first embodiment, a blade is movably coupled to the housing, the blade moving from a first position, across the opening to a second position, thereby cutting the umbilical cord which extends through the opening. The inner region of the housing engages only a portion of the umbilical cord in the housing, such that the newly cut end of the umbilical cord falls and hangs freely in the inner region, blood flowing from the umbilical cord via gravity into a blood collection region of the housing. The housing is substantially closed to the external environment, and the blood is therefore collected in a substantially aseptic environment.

In a preferred, alternative embodiment, the housing is comprised of a first portion coupled to a second portion which slideably move from a first extended position to a second collapsed position. A blade is provided on one portion of the housing, such that as the two portions are moved to the second collapsed position, the blade cuts an umbilical cord held by the housing. The newly cut end of the umbilical cord falls freely into an inner region of the housing, and blood flows from the cord via gravity into a blood collection region.

To maximize the volume of blood collected from the umbilical cord, a container is provided to receive the placenta, the container having an opening in a bottom surface to allow the umbilical cord to pass through the bottom surface of the container. In a preferred embodiment, an inflatable bladder or other means for compressing the placenta is provided, thereby forcing blood to flow from the placenta into the umbilical cord, and in turn into the blood collection region. In a preferred embodiment, a conventional blood collection bag is coupled to the housing, in fluid communication with the blood collection region, such that the blood is collected in a container in which the blood may be stored or transferred for further processing.

BRIEF DESCRIPTION OF THE DRAWINGS

FIG. 9 is a schematic illustration of a cutting blade of the apparatus of FIG. 1 shown in a first position.

FIG. 10 is a cross-sectional plan view taken along line 10—10 of FIG. 1.

FIG. 11 is a cross-sectional elevational view taken along line 11—11 of FIG. 1.

FIG. 12 is a cross-sectional plan view taken along line 12—12 of FIG. 1.

FIG. 13 is a front isometric view of a cord blood collection apparatus provided in accordance with a preferred embodiment of the present invention illustrated in a first, open position.

FIG. 13A is an enlarged, side cross-sectional elevational view of a portion of the apparatus of FIG. 13.

FIG. 14 is a top plan view of the apparatus of FIG. 13 illustrated in a closed position.

FIG. 15 is a cross-sectional plan view of the apparatus of FIG. 14.

FIG. 16 is a cross-sectional plan view of the apparatus of FIG. 15 shown in a second position.

DETAILED DESCRIPTION OF THE INVENTION

Figure 1:
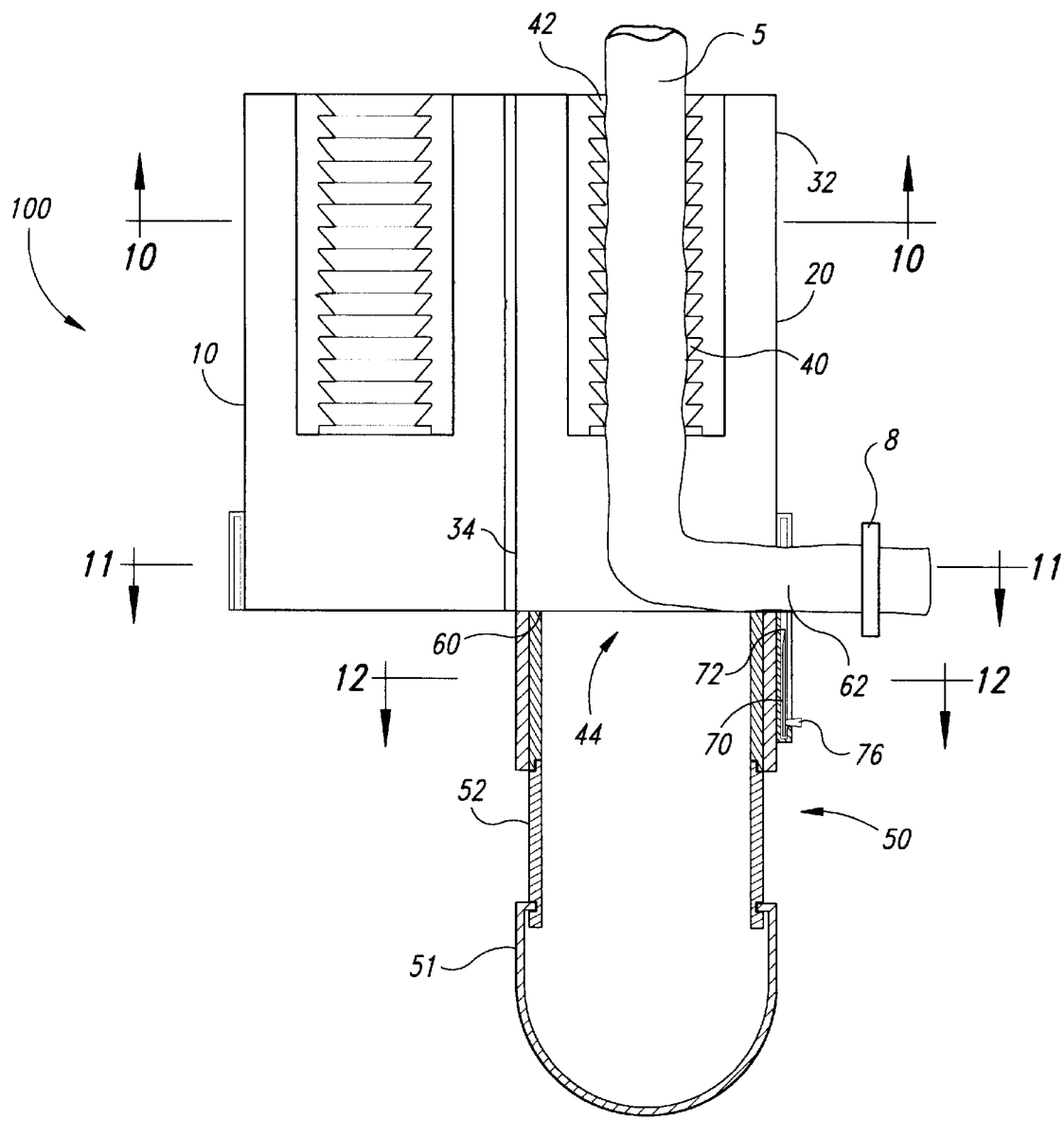
FIG. 1 is a cross-sectional front-elevational view of a cord blood collection apparatus provided in accordance with a first embodiment of the present invention prior illustrated prior to cutting of the umbilical cord.

There is a need in the art for an improved apparatus and method for collecting cord blood from an umbilical cord. In particular, it is desirable to harvest a large volume of fetal cord blood in an aseptic environment. In addition, the delivery room is a hectic environment with many tasks to be completed by the obstetrician and other delivery room personnel. The environment is also biologically diverse, with a variety of contaminants such as maternal blood and urine present on the umbilical cord and in the surrounding area. The device and method must therefore be simple to use, allowing the medical personnel to quickly and efficiently collect the umbilical cord blood in an aseptic manner. An apparatus 100 and method provided in accordance with a preferred embodiment of the present invention meet these needs.

Generally, the apparatus 100 includes a housing that can be attached to the end of an umbilical cord after the cord has been surgically detached from a baby after delivery. (After a baby is delivered, the umbilical cord is clamped and the baby is usually placed on the mother's abdomen. Typically, the cord is clamped with two Kelly clamps or a plastic umbilical cord clamp, and the cord is severed between the two clamps.) The housing contains a cutting blade that cuts the end of the umbilical cord on the placental side of the clamped cord. The cut, free end of the cord falls into a desired position in the housing, such that blood in the umbilical cord flows via gravity into a blood collection region in an aseptic environment. So placed, the apparatus of the present invention provides a barrier to prevent the movement of maternal blood, urine, and other contaminating fluids from moving along the outside of the umbilical cord into the collection region. The apparatus also shields against splashed and airborne contaminants. It is then possible for the obstetrician, once the housing has been put in place, to massage the uterine fundus prior to the time of disengagement of the placenta from the implantation site, to create a maximum pressure head over the placenta to allow for maximum volume of blood to move into the blood collection region. By massaging the uterus, the placenta is squeezed, thereby increasing the flow of blood out of the umbilical cord and into the blood collection region.

The apparatus further comprises a placenta bowl that holds the placenta for easy collection of cord blood and which further includes means for compressing the placenta in order to maximize the expulsion of blood through the umbilical cord. Together, the placenta bowl and the housing form a system that allows umbilical cord blood to be collected in an aseptic environment in a manner that is more simple and efficient than prior techniques. This system can readily be provided in the form of an aseptic kit by providing pre-sterilized individual components in aseptic enclosures, boxed for convenient storage. Such a kit would also include a cleaning composition for use in cleaning the umbilical cord in the region where it is placed into the housing of the invention; such cleaning compositions are common in the medical arts.

The invention will be better understood by reference to the figures which show a number of preferred embodiments of the invention but which are not intended to be otherwise limiting. In the figures, the same reference numbers are used throughout for corresponding parts of the device.

FIG. 1 is a cross-sectional front-elevational view of a blood collection apparatus provided in accordance with a first embodiment of the present invention. The apparatus includes a housing 100 formed from three parts, which can be separate from each other or flexibly attached to each other, or can themselves be formed from smaller separate parts. The three parts include two retaining portions and a sleeve used to collect blood.

In the embodiment shown in FIG. 1, a first retaining portion 10 and a second retaining portion 20 engage each other and together form a unified retainer 30 that engages umbilical cord 5. Unified retainer 30 has an external surface 32 and an interior channel 40 having two openings 42 and 44 to an external environment surrounding the unified retainer. The channel 40 is adapted to firmly contact an umbilical cord 5 without occluding the flow of blood through the umbilical cord. The length of the retaining portions and thus of channel 40 are selected so that the umbilical cord extends through and beyond both ends of channel 40. In a preferred embodiment, channel 40 is pre-formed, in part, in one of the retaining portions, so that the umbilical cord 5 is pushed through the pre-formed part of the channel 40 prior to being subject to the retaining action of the two retaining portions 10 and 20.

In use, a regular cord clamp 8 is placed on the umbilical cord 5 prior to cutting the cord at the time of delivery. The regular cord clamp is not part of the invention and can be any type of clamp sufficient to stop umbilical cord blood flow and that will allow placement of the cord into the device. After the cord is cut, the end of umbilical cord 5 that is clamped by clamp 8 is placed between the two retaining portions 10 and 20, and the two portions are engaged so that the umbilical cord 5 is held inside channel 40. The two openings 42 and 44 of channel 40 are respectively designated the proximal opening 42 and the distal opening 44 to show their orientation relative to the placenta coupled to the cord. A sufficient length of cord 5 extends from distal opening 44 so that the remaining operations described below can be carried out.

The third portion of the housing 100, namely, blood collection sleeve 50, engages with a lower region 34 of unified retainer 30 that surrounds distal opening 44 of channel 40. The adjacent surfaces form a junction 60 between sleeve 50 and unified retainer 30. A window 62 is present in the junction, the window being formed from a slot or slots present in either or both of the unified retainer 30 and sleeve 50. Window 62 is sized to permit passage of umbilical cord 5 through the window, as shown in FIG. 1.

As further illustrated in FIG. 1, blood collection sleeve 50 comprises upper portion 52, which engages lower portion 34 of the unified retainer 30, and lower portion 51. The upper portion 52 contains the blade assembly, and the lower portion 51 serves to collect (or funnel, if attached to an external bag) the cord blood. Sleeve upper portion 52 and sleeve lower portion 51 may be different regions of a single integral blood collection sleeve 50 or may be two separate parts which are joined together to form collection sleeve 50. By having the sleeve formed in two parts, visibility and ease of assembly of the sleeve to the unified retainer are improved.

A blade is located in one of the parts used to form housing 100. In the embodiment shown in FIG. 9, blade 70, having cutting edge 72, is located in sleeve 50 adjacent to window 62. Blade 70 is moveable and cuts umbilical cord 5 when moved in an upward direction as shown in FIG. 1. When the blade is in an upward position, blade 70 is positioned across window 62, thus isolating the interior of sleeve 50 from the external environment.

Figure 2:
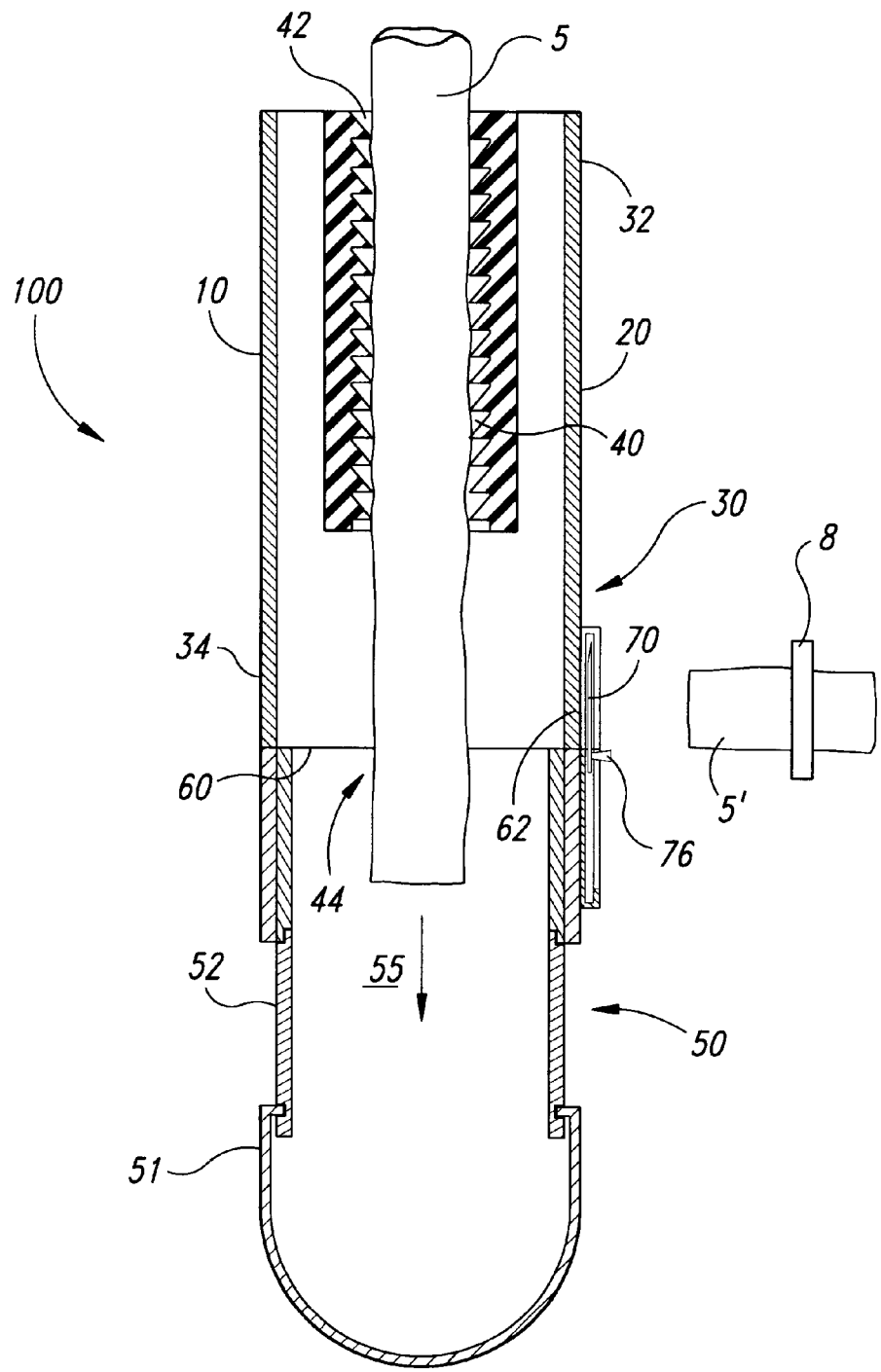
FIG. 2 is a cross-sectional front-elevational view of the apparatus of FIG. 1 illustrated after the umbilical cord is cut.

As shown in FIG. 2, movement of the blade cuts the umbilical cord for a second time, the first time being during delivery when the umbilical cord is severed to separate the placenta from the newborn so that original clamp 8 and a stump portion 5' of the terminal region of umbilical cord 5 are removed from the end of the umbilical cord. The end of the umbilical cord then falls freely and hangs in an interior region 55 of sleeve 50, such that blood flows into and collects in sleeve 50.

Figure 3:
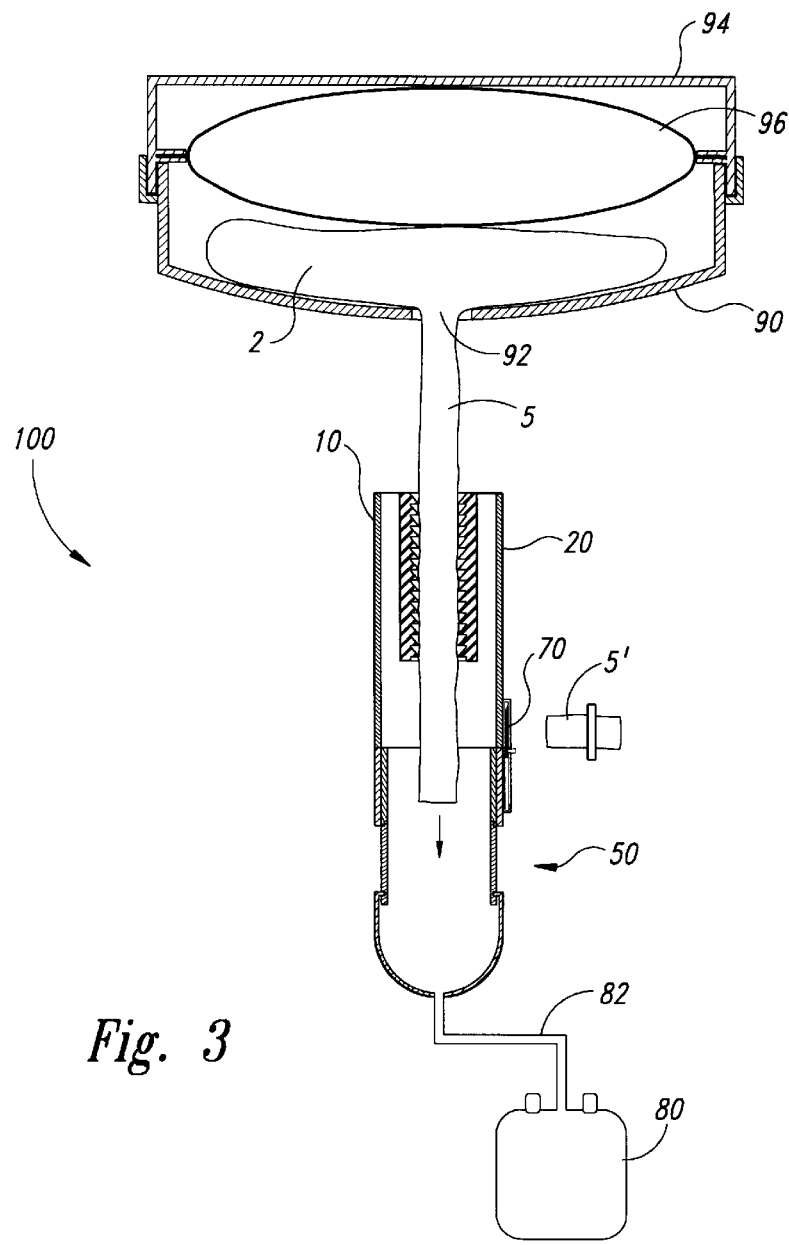
FIG. 3 is a cross-sectional front-elevational view of the cord blood collection apparatus provided in accordance with an embodiment of the present invention, incorporating the apparatus illustrated in FIG. 2.

Further components of the blood-collection system are shown in FIG. 3. The housing 100 is similar to the housing shown in FIG. 2, but the sleeve 50 is adapted so that blood is collected in an external blood collection bag 80 attached to the sleeve via tubing 82, rather than being retained in the sleeve itself.

Collection bag 80 is a conventional blood-collection bag, such as those distributed by Baxter, Fenwal Division, and is both flexible and aseptic. Flexibility of the terminal collection point of the blood collecting system is desired to prevent build up of internal back pressure when blood flows into the system. Therefore, if a large quantity of blood is collected solely in sleeve 50, sleeve 50 is desirably resilient and expandable. If sleeve 50 is formed from two separate parts, sleeve upper portion 52 and sleeve lower portion 51, then at least sleeve lower portion 51 is resilient and expandable. In a preferred embodiment, the sleeve lower portion 51 is constructed of bloodbag material coated with anticoagulant. If an expandable blood collection bag 80 is attached to the end of sleeve 50, as shown in FIG. 3, then sleeve 50 can be either resilient or rigid.

Figure 4:
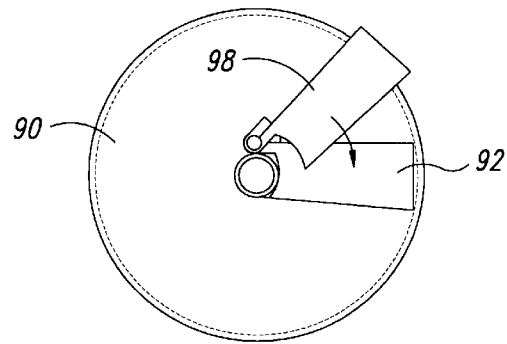
FIG. 4 is a top plan view of an element of the cord blood collection apparatus illustrated in FIG. 3.

The housing 100 is attached to a proximal end of umbilical cord 5 and is suspended by the umbilical cord from placenta 2. In a preferred embodiment, as illustrated in FIG. 3, the placenta is placed in a placenta bowl 90 that has a slot 92 which allows the umbilical cord 5 to pass through but which is sufficiently small to retain placenta 2. The slot extends from an edge of the container 90 to a gravitational low point of the container when the container is in its normal operating position. This allows blood in the placenta to flow under the influence of gravity into the umbilical cord which extends through slot 92 on the bottom of bowl 90. In an alternative embodiment, the slot 92 can be closed using slot closure arm 98 as shown in FIG. 4, while still allowing the cord to extend through the center of the container.

The system of the invention provides easy collection of placental blood under aseptic conditions, and it is possible to collect blood from the placenta and umbilical cord directly into a conventional blood-collection bag, which can then be sealed in the normal fashion at the point of entry of blood into the bag. The remaining portions of the system can then be discarded, thereby reducing the chance of biological contamination.

In an alternative embodiment also illustrated in FIG. 3, placenta bowl 90 has a cover 94 and contains an inflatable bladder 96. Inflation of bladder 96 places pressure on the placenta to both increase the rate of blood flow and to insure that the placenta drains substantially completely. It will be understood by one of ordinary skill in the art that other mechanical means for placing external pressure on the placenta, including, but not limited to, hydraulic systems, manually operated systems such as levers and screws, weights, and the like, can be used in place of the inflatable bladder 96. The inflatable bladder is used in a preferred embodiment, however, because it is relatively inexpensive and easy to manufacture.

Figure 5A:
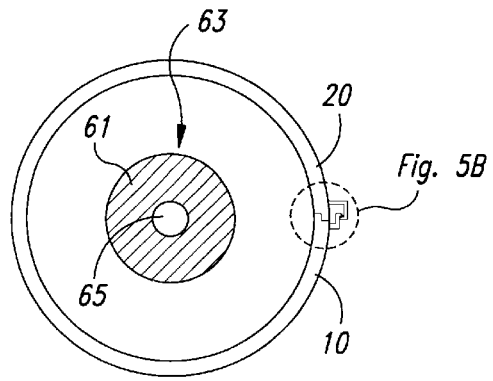
FIG. 5A is a cross-sectional plan view of the apparatus of FIG. 1.
Figure 5B:
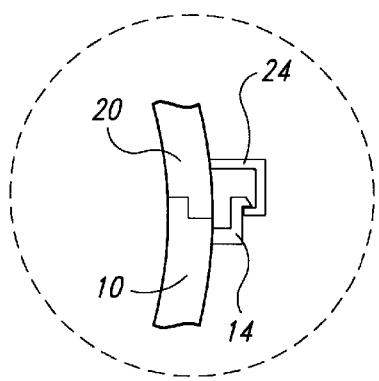
FIG. 5B is an enlarged view of a portion of the apparatus illustrated in FIG. 5A.

FIGS. 5A and 5B show one embodiment of the two retaining portions 10 and 20 and one manner in which they can be joined together. A latch 14 is present on portion 10 with a corresponding catch 24 present on portion 20. Latch 14 and catch 24 engage each other when the first and second retaining portions 10 and 20 are placed together to form unified retainer 30. In a preferred embodiment, the latches are irreversible under normal operating conditions. This can be accomplished by having the latching operation occur in an interior space so that the latch is not accessible after closure for disengagement.

Figure 6:
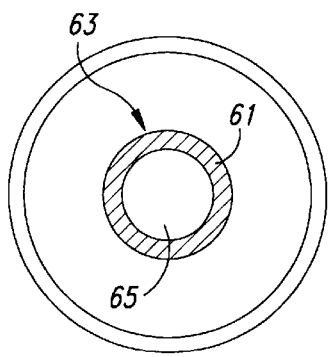
FIG. 6 is a cross-sectional plan view showing an element of the apparatus illustrated in FIG. 5A in an alternative position.

FIGS. 5A and 6 together show how a single apparatus can accommodate umbilical cords of different sizes. A semi-circular bushing 61 of resilient material, for example rubber, is present in each of the two retaining portions 10 and 20 so that when the retaining portions are brought together, the bushings form a ring-like structure 63 with an opening 65 in its center which defines channel 40 through which the umbilical cord extends. The resiliency of the bushing material is selected so that the bushing will not unduly compress the umbilical cord but will itself be compressed by the umbilical cord. As a result, the channel 40 expands as shown in FIG. 6 when an umbilical cord is placed in the channel. The resiliency is sufficient, however, so that close contact is maintained between the resilient material and the exterior surface of the umbilical cord, thus helping to prevent contaminants from passing down the exterior surface of the cord into the collected blood.

Figure 7:
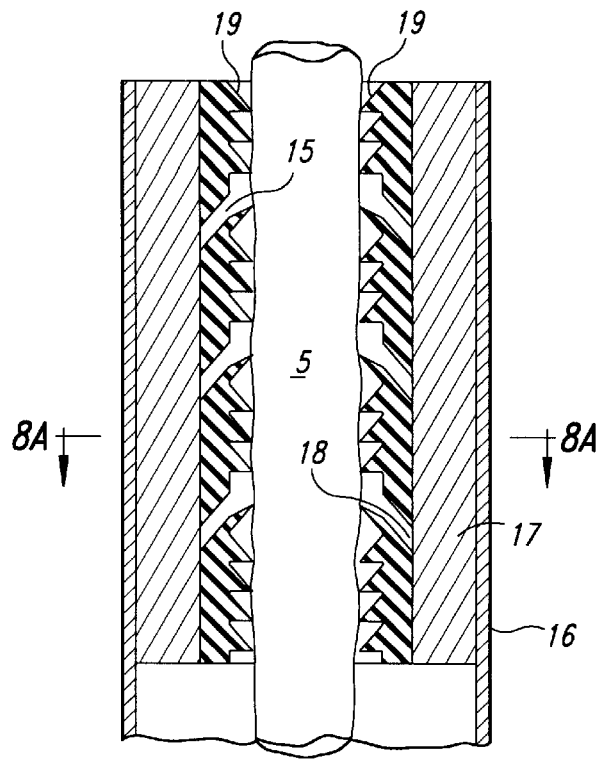
FIG. 7 is a cross-sectional front-elevational view of a portion of the apparatus illustrated in FIG. 1.
Figures 8A, 8B:
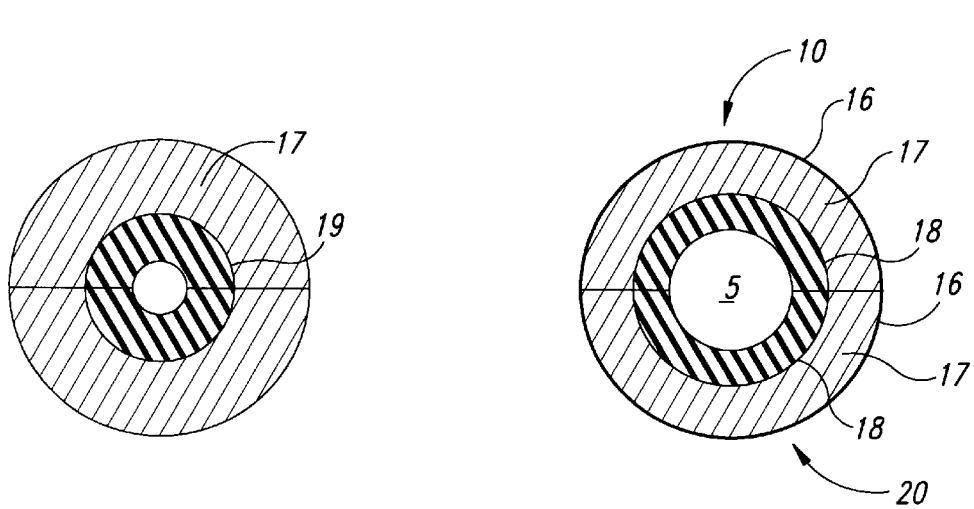
FIG. 8A is a cross-sectional plan view of the apparatus illustrated in FIG. 7, without the cord present.
FIG. 8B is a cross-sectional plan view taken along the line 8—8 of FIG. 7.
Figure 17:
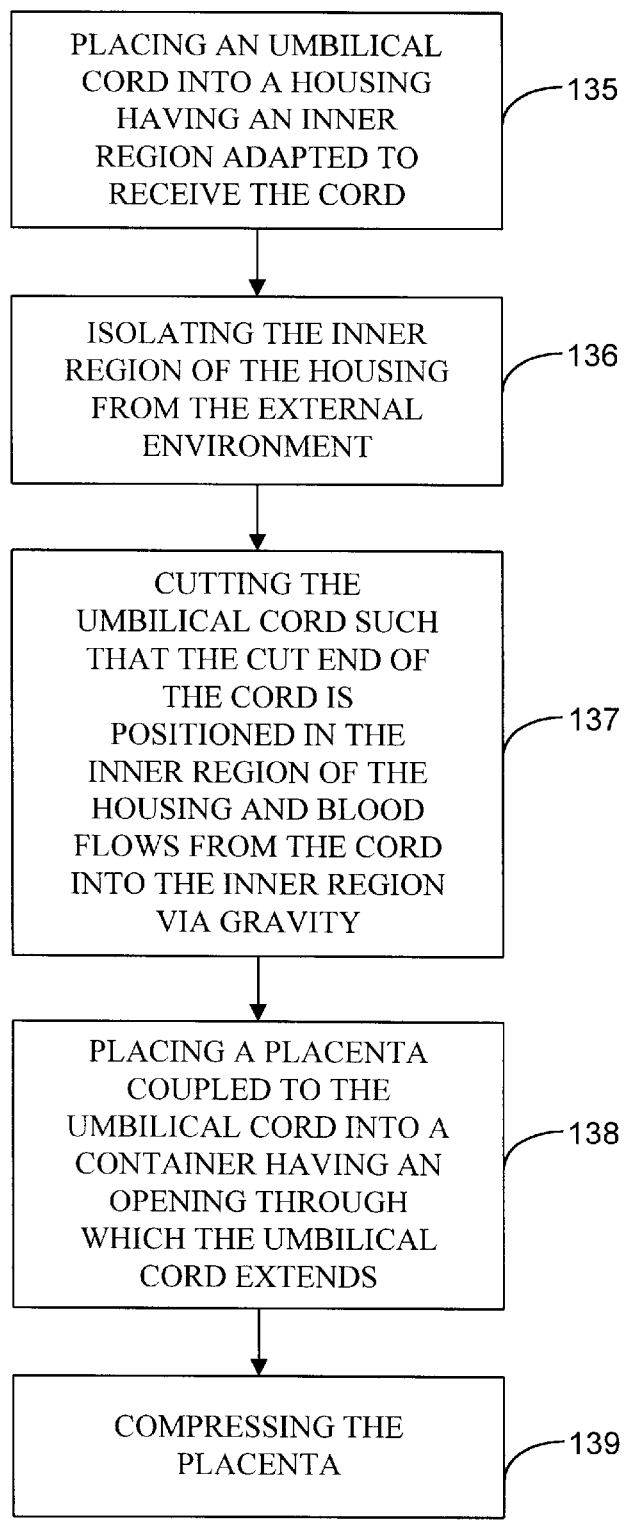
FIG. 17 is a schematic illustration of a preferred embodiment of the present invention.

FIGS. 7 and 8 illustrate an alternative embodiment of the invention in which the two retaining portions 10 and 20 are formed from three materials, namely, a rigid external shell 16, a resilient channel wall 18, and an absorbent fill material 17 positioned between the shell 16 and the channel wall 18. As can be seen in a comparison of FIG. 8A (without cord present) and FIG. 8B (with cord present), both the resilient fill material 17 and the resilient channel wall 18 are pressed outward by the cord in order to accommodate the cord without interrupting blood flow through the cord. In a preferred embodiment, by-pass channels 15 open in resilient wall 18, thereby allowing excess blood on the exterior of cord 5 to drain through channels 15 and be absorbed by resilient fill material 17.

The resilient channel wall 18 has projections 19 that mechanically engage umbilical cord 5 and prevent it from being accidentally withdrawn from the housing 100. In an alternative embodiment, retention of the cord is further achieved by two short small-gauge needles in the housing that puncture the cord upon closure of the assembly.

FIGS. 9 and 11 show details of a blade assembly used to cut off the distal end of cord 5. As discussed previously, a window is formed at junction 60 between unified retainer 30 and sleeve 50. In a preferred embodiment, one-half of the window 62 is formed in the retainer 30 and the other half of the window is formed in sleeve 50. The window 62 can have a resilient seal 64 lining its interior surface, of the same type shown in FIGS. 5A and 6. Blade 70 has a cutting edge 72 and is located in opposed grooves 54 and 55 formed in the walls of both sleeve 50 and unified retainer 30. The lower portion of grooves 54 and 55 in sleeve 50 as aligned with corresponding grooves in the unified retainer.

Sliding the blade in an upward direction causes cutting edge 72 to pass across window 62, thereby cutting the umbilical cord extending through the window.

As blade 70 moves upward, it also extends across window 62, thereby isolating the interior of the assembly from the external environment. The blade can be moved by a handle 76 attached to blade 70 than extends beyond the grooves 54 and 55. In a preferred embodiment, a latching mechanism for the handle 76 is provided in an interior region of the blade housing such that once the blade 70 is moved upward, it cannot be moved back to its original position. The cutting edge can be recessed in a wall, for example, of the sleeve, and not moved out of its recess until the umbilical cord is in position to be cut.

A number of alternative embodiments can be used to cut the umbilical cord. For example, it is possible to form the blade 70 from a wall of either the unified retainer or the sleeve 50 and to provide a sliding engagement of the unified retainer and sleeve so that engaging the two parts causes the blade to cut the umbilical cord when the umbilical cord is positioned in a desired location.

FIGS. 10–12 show three cross-sectional plan views taken along lines 10—10 11—11, and 12—12, respectively, of FIG. 1. In a preferred embodiment, the two retaining portions 10 and 20 of unified retainer 30 are held together by hinge 36 which acts to register the location of the two parts to allow the two parts to be easily assembled. However, other forms of registration, for example, corresponding pins and holes, can be provided in the two parts of the retainer.

In the cross-sectional view illustrated in FIG. 10, only the two retaining portions 10 and 20 are visible. The channel 40 will be formed from the two semi-circular grooves 40a and 40b present in the retaining portions 10 and 20, respectively.

FIG. 11 is a cross-sectional view taken at the junction between sleeve 50 and the unified retainer 30, but with unified retainer 30 shown in an open position. When retaining portion 10 is closed around hinge 36 to engage with retaining portion 20, grooves 54 and 55 in the external wall of retaining portion 10 come into alignment with grooves 54 and 55 in the sleeve. Blade 70 can then slide readily into the grooves on the upper retainer portion from its normal position in the sleeve.

FIG. 12 is a cross-sectional view taken at a lower position on sleeve 50, showing blade 70 in its normal resting position in the wall of sleeve 50.

In a preferred alternative embodiment, as illustrated in FIGS. 13–16, the blood collecting apparatus 102 is comprised of a housing 104 having a first portion 106 and a second portion 108 that are slideably movable from a first extended position 110, as illustrated in FIGS. 14 and 15, to a second collapsed position 112, as illustrated in FIG. 16.

As illustrated in FIG. 13, an upper region 120 of the housing 104 is comprised of a first piece 122 and a second piece 124 that engage each other to surround an umbilical cord 5 placed in the housing. In a preferred embodiment, the first and second pieces 122 and 124 are coupled via a continuous hinge comprised of a pliable, thin section of material extending longitudinally along the intersection between the two pieces. There is therefore no seam or gap to seal, thereby contributing to the aseptic characteristics of the device.

In a preferred embodiment, an inflatable bladder 128 is provided in the upper region of the housing, the bladder being inflatable by the introduction of a volume of gas into the bladder. This may be achieved in a variety of ways, for example, by incorporating a pump into the side of the housing, or using a manual squeeze bulb attached to a stem 105 which is in fluid communication with the bladder. In operation, an umbilical cord 5 is positioned along the length of the upper region of the housing between the first and second pieces 122 and 124, the end of the cord extending through opening 107 to a region external to the housing, as illustrated in FIG. 14. The first and second pieces 122 and 124 are closed around the cord, engaging each other to form an integral housing, as illustrated in FIG. 14. The bladder 128 is inflated to a selected pressure and then allowed to deflate to the extent that an inner surface 130 of the bladder is in contact with an outer surface of the umbilical cord, but the pressure from the bladder does not occlude the flow of blood through the cord. Because the bladder is flexible, it conforms to the diameter and irregular surface of the cord, creating a biological barrier to prevent maternal blood and other contaminants from flowing down the length of the cord into the collected blood. To further enhance the biological barrier and ensure that the bladder stays in contact with the cord as the pressure in the cord reduces, an adhesive is provided on the inner surface 130 of the bladder. In a preferred embodiment, a water-based adhesive is used. It will be understood, however, that other adhesives, such as solvent-based adhesives, two-part epoxy adhesives, and cyanoacrylate adhesives may be used. In a preferred embodiment, the section of cord enclosed by the bladder in the upper region of the housing is first wiped with alcohol and then dried, prior to being inserted into the housing.

The apparatus 102 is further provided with a plurality of projections 132 provided in an inner region 114 of the housing adjacent the bladder, the projections 132 grasping the cord and holding it in a desired location. The projections 132 are flexible enough to conform to the outer diameter of the cord without constricting the flow of blood through the cord. However, the projections 132 are also sufficiently rigid to keep the cord from sliding. The projections 132 are further configured to accommodate and grasp cords of various diameters, without constricting the flow of blood. As illustrated in FIGS. 15 and 16, each of the projections 132 has a slightly tapered thickness.

As illustrated in FIG. 14, a blade 116 is coupled to the first portion 106 of the housing, such that when the first portion 106 and second portion 108 are moved to the second collapsed position 112, the blade 116 cuts the umbilical cord 5 extending through opening 107. In a preferred embodiment, a standard double-bevel, mini-utility blade, such as those sold by American Safety Razor Company, is used. As a result, the newly cut end of the umbilical cord falls and hangs freely in the inner region 114 of the housing, as illustrated in FIG. 16. In a preferred embodiment, as illustrated in FIGS. 13 and 13A, a support 113 is coupled to bracket 111 behind the umbilical cord 5, relative to the blade 116. Support 113 is made of an elastomeric material, such as C-Flex, Kraton, or other synthetic rubber. As illustrated in FIG. 13A, the blade 116 cuts through the cord 5, and through a bottom section of the support 113. In this manner, the blade cuts cleanly and completely through the cord.

Once cut, blood from the placenta and umbilical cord is then free to flow via gravity through one-way valve 134 into blood collection region 118. The one-way valve 134 helps prevent the collected blood from contacting the exterior of the umbilical cord, and reduces the chance of leakage of the collected blood. In a preferred embodiment, an interior surface of the one-way valve 134 and blood collection region 118 is covered with a conventional anticoagulant, such as a heparin coating. A conventional blood bag containing anticoagulant is coupled to the blood collection region 118 via conventional tubing coupled to the septum 109.

As illustrated in FIGS. 15 and 16, a locking mechanism 126 and corresponding locking holes 127 are provided in a side region of the housing, such that when the first and second portions of the housing are moved to the second collapsed position 112, the locking mechanism 126 engages holes 127, thereby preventing the device from being inadvertently opened. Prior to being attached to a cord, the tabs 111 are positioned in aperture 113. When the first and second pieces 122 and 124 are closed, the tabs 111 are depressed, thereby allowing the second portion 108 of the housing to slide towards the first portion 106. The first and second portions 106 and 108 cannot be slid together, which would expose the blade, until the first and second pieces 122 and 124 are engaged. The blade therefore is never exposed to the user, thereby reducing the risk of accidental cuts. In an alternative embodiment, the apparatus 102 is provided with ratchets so that the mechanism can move in only a single direction, preventing the device from being collapsed part way, thereby partially cutting the cord, and then accidentally re-extended.

The exterior surface of the housing is ribbed, allowing the user to grasp it firmly. As the first and second portions are collapsed together, the opening 107 is closed, thereby maintaining the aseptic condition, and allowing the volume of blood to be collected in an aseptic environment. A large quantity of blood may therefore be collected from an umbilical cord in an aseptic manner using an apparatus provided in accordance with a preferred embodiment of the present invention, by placing an umbilical cord 5 into a housing having an inner region adapted to receive the cord, step 135. The inner region of the housing is isolated from the external environment, step 136, thereby allowing the collection to proceed in an aseptic environment. The umbilical cord is cut such that the cut end of the cord is positioned in the inner region of the housing adjacent a blood collection region, step 137, and blood flows from the cord into the blood collection region via gravity. To maximize the volume of blood collected, the placenta coupled to the umbilical cord is placed in a container having an opening through which the umbilical cord extends, step 138, and the placenta is compressed, step 139.

An apparatus and method for collecting blood from an umbilical cord has been shown and described. From the foregoing, it will be appreciated that although embodiments of the invention have been described herein for purposes of illustration, various modifications may be made without deviating from the spirit of the invention. Thus, the present invention is not limited to the embodiments described herein, but rather is described by the claims that follow.

We claim:

1. An apparatus for collecting blood from an umbilical cord, comprising:
   a housing having a channel in an inner region, the housing having an opening in communication with the channel and in communication with a region external to the housing, the channel adapted to allow the umbilical cord to pass therethrough and extend through the opening;
   a blade moveably coupled to the housing, the blade being positioned to move from a first position, across the opening to a second position, thereby cutting the umbilical cord extending through the opening, the inner region of the housing engaging only a portion of the umbilical cord such that an end of the umbilical cord hangs freely in the inner region; and
   a blood collection region in fluid communication with the inner region of the housing, such that blood flows via gravity from the umbilical cord into the blood collection region, the housing being substantially closed to the external environment such that the blood from the umbilical cord is collected in a substantially aseptic environment.

2. The apparatus according to claim 1 wherein the housing further comprises a first piece and a second piece, the first and second pieces engaging each other after the umbilical cord is placed between the first and second pieces, thereby surrounding the umbilical cord.

3. The apparatus according to claim 2 wherein the first and second pieces are hingedly connected.

4. The apparatus according to claim 2 wherein a locking mechanism is provided on the housing such that the first and second pieces are lockingly engaged.

5. The apparatus according to claim 2 wherein the first and second pieces are matingly engaged.

6. The apparatus according to claim 2 wherein the first and second pieces are each formed from a rigid external shell, a resilient channel wall, and a resilient, porous fill material provided between the shell and the channel wall.

7. The apparatus according to claim 1, further comprising opposed grooves provided in an outer surface of the housing adjacent to the opening, the blade moving from the first position to the second position by sliding in the grooves.

8. The apparatus according to claim 1, further comprising an inflatable bladder positioned in the inner region of the housing concentric with the channel, a volume of gas being provided to inflate the bladder, such that an inner surface of the bladder is adjacent to an outer surface of the umbilical cord.

9. The apparatus according to claim 8 wherein an adhesive is provided on the inner surface of the bladder.

10. The apparatus according to claim 1, further comprising a plurality of resilient projections provided on an inner wall of the channel, the resilient projections grasping and holding the umbilical cord in a desired location.

11. The apparatus according to claim 1, further comprising a one-way valve positioned in the housing in fluid communication with the inner region and the blood collection region.

12. The apparatus according to claim 1, further comprising a resilient bloodbag coupled to the blood collection region of the housing.

13. The apparatus according to claim 1 wherein the blood collection region is flexible.

14. The apparatus according to claim 1, further comprising a container coupled to the housing, the container receiving a placenta and having an opening through which the umbilical cord extends.

15. The apparatus according to claim 14, further comprising means for compressing the placenta in the container.

16. The apparatus according to claim 14 wherein the container has a cover which isolates an inner region of the container from the environment external to the container.

17. An apparatus for collecting blood from an umbilical cord, comprising:
a housing having a first portion and a second portion, the first and second portions being slideably moveable from a first extended position to a second collapsed position;
a blade coupled to the first portion of the housing, the blade cutting an umbilical cord held by the housing when the first and second portions are slideably moved to the second collapsed position, the cut end of the umbilical cord falling freely into an inner region of the housing; and
a blood collection region in fluid communication with the inner region such that blood flows from the umbilical cord into the blood collection region via gravity.

18. The apparatus according to claim 17 wherein an upper region of the housing further comprises a first piece and a second piece, the first and second pieces engaging each other after the umbilical cord is placed between the first and second pieces, thereby surrounding the umbilical cord.

19. The apparatus according to claim 18 wherein the first and second pieces are hingedly connected.

20. The apparatus according to claim 18 wherein a locking mechanism is provided on the housing such that the first and second pieces are lockingly engaged.

21. The apparatus according to claim 18, further comprising a locking mechanism that prevents the first and second portions from being moved to the second collapsed position until the first and second pieces are engaged, thereby preventing the user from being exposed to the blade.

22. The apparatus according to claim 18 wherein the first and second pieces are matingly engaged.

23. The apparatus according to claim 17, further comprising an inflatable bladder positioned in the inner region of the housing concentric to a channel extending longitudinally through an upper region of the housing, a volume of gas being provided to inflate the bladder such that an inner surface of the bladder is adjacent to an outer surface of the umbilical cord extending through the channel.

24. The apparatus according to claim 23 wherein an adhesive is provided on the inner surface of the bladder.

25. The apparatus according to claim 23, further comprising a plurality of resilient projections provided on an inner wall of the channel adjacent to the inflatable bladder, the resilient projections grasping and holding the umbilical cord in a desired location.

26. The apparatus according to claim 17, further comprising a plurality of resilient projections provided on an inner wall of a channel extending through an upper region of the housing, the resilient projections grasping and holding the umbilical cord in a desired position.

27. The apparatus according to claim 17, further comprising a one-way valve positioned in the housing in fluid communication with the inner region and the blood collection region.

28. The apparatus according to claim 17, further comprising a resilient bloodbag coupled to the blood collection region.

29. The apparatus according to claim 17, further comprising an anticoagulant coating provided on an inner surface of the blood collection region.

30. The apparatus according to claim 17, further comprising a container, the container receiving a placenta and having an opening through which the umbilical cord extends.

31. The apparatus according to claim 30, further comprising means for compressing the placenta in the container.

32. The apparatus according to claim 17, further comprising a support coupled to the housing such that when the umbilical cord is held by the housing, the cord is positioned between the blade and the support.

33. An apparatus for collecting blood from an umbilical cord, comprising:
a housing having a first portion and a second portion, the first and second portions being slideably moveable from a first extended position to a second collapsed position;
a blade coupled to the first portion of the housing, the blade cutting an umbilical cord held by the housing when the first and second portions are slideably moved to the second collapsed position, the cut end of the umbilical cord falling freely into an inner region of the housing;
a blood collection region in fluid communication with the inner region such that blood flows from the umbilical cord into the blood collection region via gravity;
an upper region of the housing further comprises a first piece and a second piece, the first and second pieces engaging each other after the umbilical cord is placed between the first and second pieces, thereby surrounding the umbilical cord, a locking mechanism being provided on the housing such that the first and second pieces lockingly engage;
an inflatable bladder positioned in the inner region of the housing concentric to a channel extending longitudinally through an upper region of the housing, a volume of gas being provided to inflate the bladder such that an inner surface of the bladder is adjacent to an outer surface of the umbilical cord extending through the channel; and
a plurality of resilient projections provided on an inner wall of the channel adjacent to the inflatable bladder, the resilient projections grasping and holding the umbilical cord in a desired location.

34. The apparatus according to claim 33, further comprising a one-way valve positioned in the housing in fluid communication with the inner region and the blood collection region.

35. The apparatus according to claim 33 wherein an adhesive is provided on the inner surface of the bladder.

36. The apparatus according to claim 33, further comprising a resilient bloodbag coupled to the blood collection region.

37. The apparatus according to claim 36, further comprising an anticoagulant coating provided on an inner surface of the bloodbag and the blood collection region.

38. The apparatus according to claim 33, further comprising a container, the container receiving a placenta and having an opening through which the umbilical cord extends.

39. The apparatus according to claim 33, further comprising a locking mechanism that prevents the first and second portions from being moved to the second collapsed position until the first and second pieces are engaged, thereby preventing the user from being exposed to the blade.

40. A method for collecting a volume of blood from an umbilical cord in an aseptic environment, comprising:
placing the umbilical cord into a housing having a first portion and a second portion, the first and second portions being slideably movable from a first extended position to a second collapsed position, the first portion further comprising a first piece and a second piece that engage each other to surround the umbilical cord;

closing the first and second piece of the housing to surround the umbilical cord;

inflating a bladder positioned in an inner region of the housing concentric to a channel extending longitudinally through an upper region of the housing, such that the bladder comes into contact with, and conforms to, an outer surface of the umbilical cord; and sliding the first and second portions of the housing from the first extended position to the second collapsed position, thereby cutting the umbilical cord via a blade coupled to the housing, the cut end of the umbilical cord falling freely into the inner region of the housing, blood flowing via gravity from the umbilical cord into a blood collection region.

\* \* \* \* \*